(12) United States Patent
Shi et al.

(10) Patent No.: US 11,964,969 B2
(45) Date of Patent: Apr. 23, 2024

(54) CRYSTAL FORMS OF THIAZOLE COMPOUND AND APPLICATION THEREOF

(71) Applicant: PHAENO THERAPEUTICS CO., LTD, Zhejiang (CN)

(72) Inventors: Weihua Shi, Shanghai (CN); Zhigan Jiang, Shanghai (CN); Haiying He, Shanghai (CN)

(73) Assignee: PHAENO THERAPEUTICS CO., LTD, Hangzhou (CN)

( * ) Notice: Subject to any disclaimer, the term of this patent is extended or adjusted under 35 U.S.C. 154(b) by 652 days.

(21) Appl. No.: 17/258,011

(22) PCT Filed: Jul. 5, 2019

(86) PCT No.: PCT/CN2019/094824
§ 371 (c)(1),
(2) Date: Jan. 5, 2021

(87) PCT Pub. No.: WO2020/007355
PCT Pub. Date: Jan. 9, 2020

(65) Prior Publication Data
US 2021/0276993 A1 Sep. 9, 2021
US 2023/0132370 A9 Apr. 27, 2023

(30) Foreign Application Priority Data

Jul. 6, 2018 (CN) .................. 201810738963.X

(51) Int. Cl.
*C07D 417/12* (2006.01)
*A61P 31/22* (2006.01)
(52) U.S. Cl.
CPC ............ *C07D 417/12* (2013.01); *A61P 31/22* (2018.01); *C07B 2200/13* (2013.01)
(58) Field of Classification Search
CPC .......................... C07D 417/12; A61K 31/426
See application file for complete search history.

(56) References Cited

U.S. PATENT DOCUMENTS

| | | |
|---|---|---|
| 7,105,553 B2 | 9/2006 | Fischer et al. |
| 7,361,659 B2 | 4/2008 | Gatti McArthur et al. |
| 8,784,887 B2 | 7/2014 | Laich et al. |
| 10,647,710 B2 | 5/2020 | He et al. |

FOREIGN PATENT DOCUMENTS

| | | |
|---|---|---|
| DE | 10226048 A1 | 12/2003 |
| JP | 2014-528948 A | 10/2014 |
| WO | WO 2018/127207 * | 7/2018 |

OTHER PUBLICATIONS

Adeyeye, Moji, ed., Preformulation in Solid Dosage Form Development (Informa Healthcare, 2008) Chapter 2.3, pp. 63-80.*
Bastin et al., Organic Process Research & Development 2000, 4, 427-435.*
Gould, International J. of Therapeutics 33, 201-213 (1986).*
Liu, Rong, ed., Water-Insoluble Drug Formulation (CRC Press, 2008) Chapter 15 pp. 417-435.*
Morris, et al., International Journal of Pharmaceutics 105 (1994) 209-217.*
Serajuddin, Advanced Drug Delivery Reviews 59 (2007) 603-616.*
Swarbrick et al., eds. Encyclopedia of Pharmaceutical Technology 13 (Marcel Dekker, NY 1996) pp. 453-499.*

* cited by examiner

*Primary Examiner* — Deepak R Rao
(74) *Attorney, Agent, or Firm* — Mintz Levin Cohn Ferris Glovsky and Popeo, P.C.

(57) ABSTRACT

Disclosed by the present invention are a crystal form A of a compound represented by formula (I), a compound represented by formula (II) and a crystal form B thereof, as well as an application of the crystal form A of the compound represented by formula (I), the compound represented by formula (II) and the crystal form B thereof in the preparation of a drug for the treatment diseases associated with the herpes simplex virus.

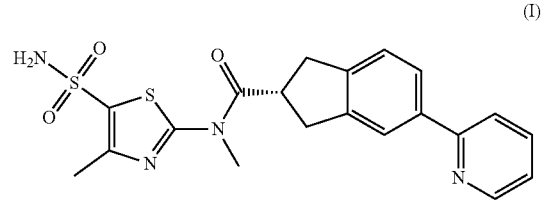

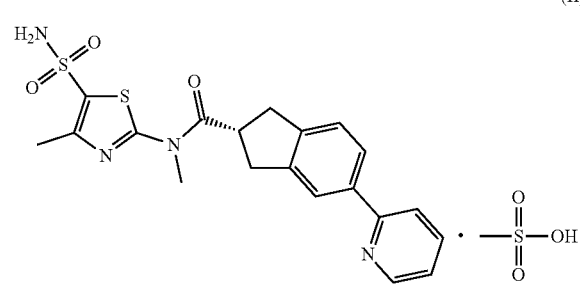

18 Claims, 4 Drawing Sheets

CRYSTAL FORMS OF THIAZOLE COMPOUND AND APPLICATION THEREOF

The present application is a United States National Phase under 35 U.S.C. § 371 of International Application No. PCT/CN2019/094824, filed Jul. 5, 2019, which claims the priority of Chinese Patent Application No. CN201810738963.X, filed on Jul. 6, 2018. The entire contents of both prior applications are hereby incorporated by reference for all purposes.

FIELD OF THE INVENTION

The present disclosure relates to a crystal form A of a compound of formula (I), a compound of formula (II) and a crystal form B thereof, and use of the crystal form A of a compound of formula (I), the compound of formula (II) and the crystal form B thereof in the preparation of a medicament for the treatment of diseases related to herpes simplex virus.

BACKGROUND OF THE INVENTION

There is a great demand for new treatment methods in the treatment of viral diseases. Although great progress has been made in the development of treatment methods for various bacterial infections, there are few viable methods for the treatment of viruses. Zidovudine is the main species that has been approved for the treatment of human immunodeficiency virus. Ganciclovir, acyclovir and foscarnet are currently used to treat herpes virus infections. However, these treatment methods have considerable side effects because they damage the DNA replication of host cells or only have an effect on a limited number of viral infections. In addition, it is known that viruses can develop resistance to treatment, making the effect of the treatment increasingly declining.

The herpesviridae is a family of DNA viruses, including herpes simplex virus-1 (HSV-1), herpes simplex virus-2 (HSV-2), cytomegalovirus (CMV), varicella-zoster virus (VZV), Epstein-Barr virus, human herpes virus-6 (HHV6), human herpes virus-7 (HHV7), human herpes virus-8 (HHV8), pseudorabies virus and rhinotracheitis virus, etc.

SUMMARY OF THE INVENTION

The present disclosure provides the X-ray powder diffraction pattern of the crystal form A of the compound of formula (I) having characteristic diffraction peaks at the following 2θ angles: 10.81±0.2°, 15.97±0.2°, and 21.69±0.2°.

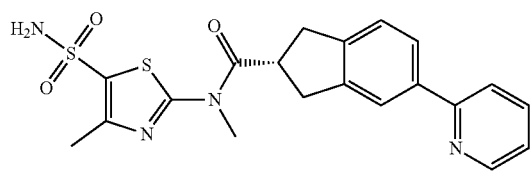

(I)

In some embodiments of the present disclosure, the X-ray powder diffraction pattern of the crystal form A described above has characteristic diffraction peaks at the following 2θ angles: 10.81±0.2°, 13.03±0.2°, 15.97±0.2°, 18.48±0.2°, 21.69±0.2°, 23.78±0.2°, 25.14±0.2°, and 26.96±0.2°.

In some embodiments of the present disclosure, the X-ray powder diffraction pattern of the crystal form A described above has characteristic diffraction peaks at the following 2θ angles: 6.581°, 10.807°, 13.031°, 15.301°, 15.637°, 15.971°, 17.253°, 18.160°, 18.475°, 20.076°, 20.644°, 21.688°, 22.381°, 23.782°, 25.141°, 26.167°, 26.959°, 29.108°, 31.492°, 31.904°, 32.061°, 33.385°, and 36.623°.

In some embodiments of the present disclosure, the XRPD pattern of the crystal form A described above is shown in FIG. 1.

In some embodiments of the present disclosure, the analytical data of the XRPD pattern of the crystal form A described above is shown in Table 1.

TABLE 1

Analytical data of the XRPD pattern of the crystal form A

| No. | Diffraction angle 2θ (°) | Relative intensity (%) |
| --- | --- | --- |
| 1 | 6.581 | 15.2 |
| 2 | 10.807 | 42.3 |
| 3 | 13.031 | 17.7 |
| 4 | 15.301 | 54.1 |
| 5 | 15.637 | 97.9 |
| 6 | 15.971 | 100.0 |
| 7 | 17.253 | 16.3 |
| 8 | 18.160 | 44.0 |
| 9 | 18.475 | 47.9 |
| 10 | 20.076 | 31.0 |
| 11 | 20.644 | 24.6 |
| 12 | 21.688 | 86.5 |
| 13 | 22.381 | 29.7 |
| 14 | 23.782 | 60.1 |
| 15 | 25.141 | 44.3 |
| 16 | 26.167 | 21.4 |
| 17 | 26.959 | 42.4 |
| 18 | 29.108 | 12.9 |
| 19 | 31.492 | 14.8 |
| 20 | 31.904 | 7.5 |
| 21 | 32.061 | 7.1 |
| 22 | 33.385 | 11.5 |
| 23 | 36.623 | 7.4 |

In some embodiments of the present disclosure, the differential scanning calorimetry (DSC) curve of the crystal form A described above has a starting point of the endothermic peak at 216.04±3° C.

In some embodiments of the present disclosure, the DSC curve of the crystal form A described above is shown in FIG. 2.

In some embodiments of the present disclosure, the thermogravimetric analysis (TGA) curve of the crystal form A described above has a weight loss of up to 0.4442% at 120±3° C. and up to 2.4492% at 204±3° C.

In some embodiments of the present disclosure, the TGA curve of the crystal form A described above is shown in FIG. 3.

The present disclosure also provides a compound of formula (II),

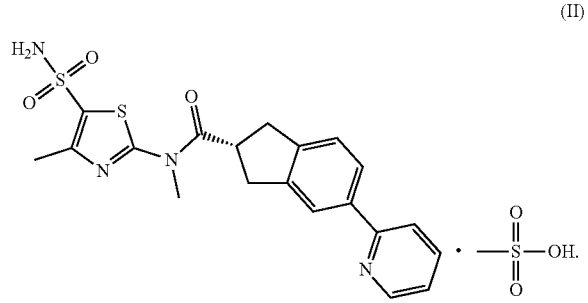

(II)

The present disclosure also provides the X-ray powder diffraction pattern of the crystal form B of the compound of formula (II) having characteristic diffraction peaks at the following 2θ angles: 10.17±0.2°, 11.85±0.2°, and 15.94±0.2°.

In some embodiments of the present disclosure, the X-ray powder diffraction pattern of the crystal form B described above has characteristic diffraction peaks at the following 2θ angles: 8.46±0.2°, 10.17±0.2°, 11.85±0.2°, 13.98±0.2°, 15.94±0.2°, 20.39±0.2°, 21.32±0.2°, and 23.78±0.2°.

In some embodiments of the present disclosure, the X-ray powder diffraction pattern of the crystal form B described above has characteristic diffraction peaks at the following 2θ angles: 8.460°, 10.174°, 11.535°, 11.850°, 13.982°, 15.935°, 19.110°, 19.464°, 19.939°, 20.391°, 21.888°, 23.309°, 23.780°, 24.517°, 24.929°, 26.034°, 26.367°, 26.959°, 27.352°, 28.772°, 30.626°, 31.297°, 32.067°, 33.845°, and 38.235°.

In some embodiments of the present disclosure, the XRPD pattern of the crystal form B described above is shown in FIG. 4.

In some embodiments of the present disclosure, the analytical data of the XRPD pattern of the crystal form B described above is shown in Table 2.

TABLE 2

Analytical data of the XRPD pattern of the crystal form B

| No. | Diffraction angle 2θ (°) | Relative intensity (%) |
| --- | --- | --- |
| 1 | 8.460 | 23.1 |
| 2 | 10.174 | 62.4 |
| 3 | 11.535 | 13.0 |
| 4 | 11.850 | 63.1 |
| 5 | 13.982 | 51.7 |
| 6 | 15.935 | 91.8 |
| 7 | 19.110 | 13.9 |
| 8 | 19.464 | 32.8 |
| 9 | 19.939 | 34.5 |
| 10 | 20.391 | 44.2 |
| 11 | 21.319 | 57.5 |
| 12 | 21.888 | 22.3 |
| 13 | 23.309 | 68.8 |
| 14 | 23.780 | 100.0 |
| 15 | 24.517 | 10.4 |
| 16 | 24.929 | 22.0 |
| 17 | 26.034 | 10.8 |
| 18 | 26.367 | 10.2 |
| 19 | 26.959 | 22.3 |
| 20 | 27.352 | 16.4 |
| 21 | 28.772 | 11.3 |

TABLE 2-continued

Analytical data of the XRPD pattern of the crystal form B

| No. | Diffraction angle 2θ (°) | Relative intensity (%) |
| --- | --- | --- |
| 22 | 30.626 | 25.0 |
| 23 | 31.297 | 12.3 |
| 24 | 32.067 | 21.6 |
| 25 | 33.845 | 13.5 |
| 26 | 38.235 | 12.0 |

In some embodiments of the present disclosure, the differential scanning calorimetry (DSC) curve of the crystal form B described above has a starting point of the endothermic peak at 185.89±3° C.

In some embodiments of the present disclosure, the DSC curve of the crystal form B described above is shown in FIG. 5.

In some embodiments of the present disclosure, the thermogravimetric analysis (TGA) curve of the crystal form B described above has a weight loss of up to 0.7160% at 187.16±3° C.

In some embodiments of the present disclosure, the TGA curve of the crystal form B described above is shown in FIG. 6.

The present disclosure also provides a use of the crystal form A described above in the preparation of a medicament for the treatment of diseases related to herpes simplex virus.

The present disclosure also provides a use of the compound of formula (II) and the crystal form B thereof described above in the preparation of a medicament for the treatment of diseases related to herpes simplex virus.

Technical Effects

As a novel thiazole compound, the compound of the present disclosure has good antiviral activity against herpes simplex virus (HSV); and shows lower plasma exposure and better safety at the same effective dose in the pharmacokinetic study in vivo. The crystal form A of the compound of formula (I) and the crystal form B of the compound of formula (II) disclosed herein are stable, are less affected by light, heat and humidity, and have good efficacy for in vivo administration, thereby having broad prospect of druggability.

Definition and Description

Unless otherwise stated, the following terms and phrases used herein are intended to have the following meanings. A specific phrase or term should not be considered uncertain or unclear without a specific definition, but should be understood in the ordinary sense. When a trade name appears herein, it is intended to refer to the corresponding commodity or the active ingredient thereof.

The intermediate compounds of the present disclosure can be prepared by a variety of synthetic methods well known to those skilled in the art, including the specific embodiments listed below, the embodiments formed by combining them with other chemical synthetic methods, and the equivalent alternative methods well known to those skilled in the art. The preferred embodiments include, but are not limited to, the examples of the present disclosure.

The chemical reactions in the specific embodiments disclosed herein are completed in a suitable solvent, which must be suitable for the chemical changes of the present disclosure and the reagents and materials required. In order to obtain the compound of the present disclosure, it is sometimes necessary for those skilled in the art to modify or select synthetic steps or reaction schemes based on the existing embodiments.

The present disclosure will be described in detail below through examples, which are not intended to limit the present disclosure.

All solvents used in the present disclosure are commercially available and can be used without further purification.

All solvents used in the present disclosure are commercially available. The present disclosure uses the following abbreviations: EtOH stands for ethanol; MeOH stands for methanol; TFA stands for trifluoroacetic acid; TsOH stands for p-toluenesulfonic acid; mp stands for melting point; EtSO$_3$H stands for ethanesulfonic acid; MeSO$_3$H stands for methanesulfonic acid; THF stands for tetrahydrofuran; EtOAc stands for ethyl acetate; NBS stands for N-bromosuccinimide; AIBN stands for azobisisobutyronitrile; DMSO stands for dimethyl sulfoxide; DMF stands for N,N-dimethylformamide; EDCI stands for carbodiimide; and HOBt stands for 1-hydroxybenzotriazole.

X-Ray Powder Diffraction (XRPD) Method Used in the Present Disclosure

Instrument model: Bruker D8 advance X-ray diffractometer

Test method: About 10 to 20 mg of sample was used for XRPD analysis.

The detailed XRPD parameters were as follows:
Light tube: Cu, kα, (λ=1.54056 Å).
Voltage of the light tube: 40 kV, current of the light tube: 40 mA
Divergence slit: 0.60 mm
Detector slit: 10.50 mm
Anti-scatter slit: 7.10 mm
Scanning range: 4-40 deg
Step size: 0.02 deg
Step length: 0.12 second
Rotation speed of sample disk: 15 rpm Differential Scanning Calorimetry (DSC) Method Used in the Present Disclosure Instrument model: TA Q2000 Differential Scanning calorimeter Test method: The sample (~1 mg) was taken and put into a DSC aluminum pot for testing. Under the condition of 50 mL/min N$_2$, the sample was heated from 30° C. (room temperature) to 300° C. (or 350° C.) at a heating rate of 10° C./min.

Thermogravimetric Analysis (TGA) Method Used in the Present Disclosure

Instrument model: TA Q5000IR Thermogravimeter

Test method: The sample (2 to 5 mg) was taken and put into a TGA platinum pot for testing. Under the condition of 25 mL/min N$_2$, the sample was heated from room temperature to 300° C. or 20% weight loss at a heating rate of 10° C./min.

Dynamic Vapor Sorption (DVS) Method Used in the Present Disclosure

Instrument model: SMS DVS Advantage dynamic vapor sorption apparatus

Test condition: The sample (10~15 mg) was taken and put into a DVS sample pan for testing.

The detailed DVS parameters were as follows:
Temperature: 25° C.
Equilibration: dm/dt=0.01%/min (The shortest time: 10 min, and the longest time: 180 min)

Drying: Dried for 120 min at 0% RH
RH (%) test gradient: 10%
Range of RH (%) test gradient: 0%-90%-0%
The classification of hygroscopicity evaluation was as follows:

| Classification of hygroscopicity | Weight increase by moisture absorption* |
|---|---|
| Deliquescence | Absorb enough water and form a liquid |
| Very hygroscopic | ΔW % ≥ 15% |
| Hygroscopic | 15% > ΔW % ≥ 2% |
| Slightly hygroscopic | 2% > ΔW % ≥ 0.2% |
| No or almost no hygroscopicity | ΔW % < 0.2% |

*Weight increase by moisture absorption at 25 ± 1° C. and 80 ± 2% RH

DETAILED DESCRIPTION OF THE INVENTION

Figure 1:
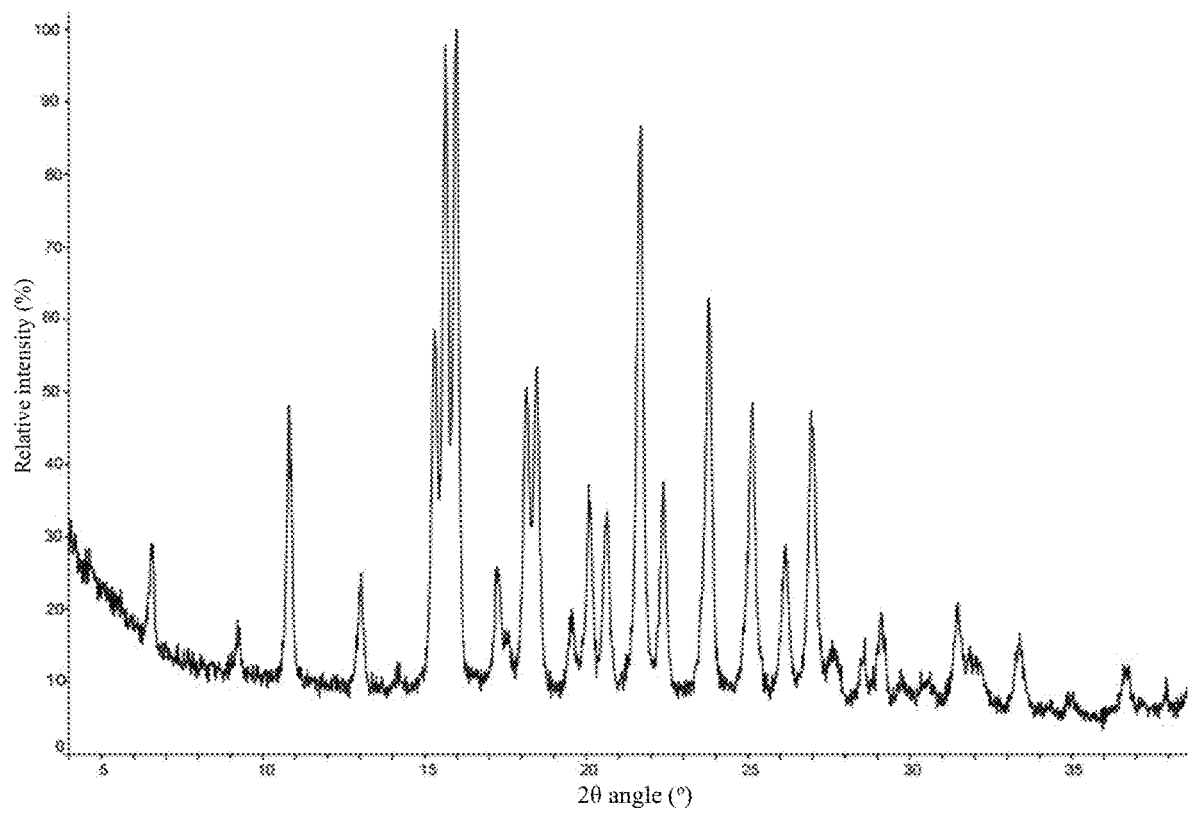
FIG. 1 is the XRPD pattern of the crystal form A of the compound of formula (I) using Cu-Kα radiation.

In order to better understand the content of the present disclosure, the present disclosure is further illustrated below in conjunction with specific examples, but the specific embodiments are not intended to limit the content of the present disclosure.

Example 1: Preparation of the Compound of Formula (I)

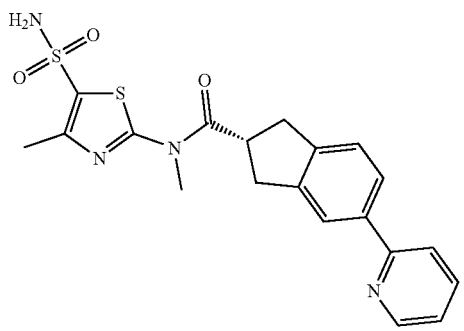

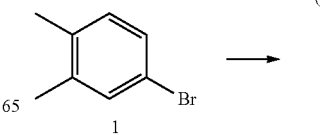

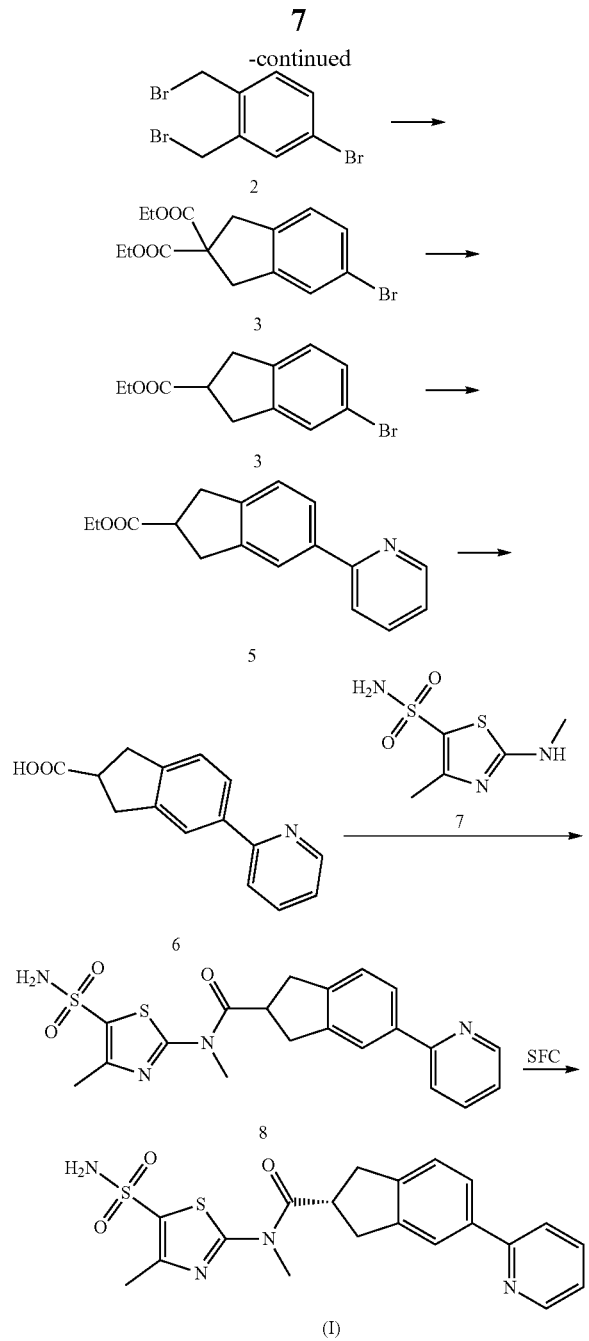

Step 1: Synthesis of the Compound 2

To a solution of the compound 1 (30.00 g, 162.11 mmol) in carbon tetrachloride (400.00 mL) were added NBS (57.70 g, 324.22 mmol) and AIBN (5.32 g, 32.42 mmol), and the system was stirred at 80° C. for 2 hours. After the reaction was completed, the reaction mixture was concentrated under reduced pressure, and the residue was purified by column chromatography to give the compound 2 as a colorless oil. $^1$H NMR (400 MHz, CDCl$_3$) δ 7.55 (s, 1H), 7.47-7.45 (m, 1H), 7.28-7.25 (m, 1H), 4.62 (s, 1H), 4.60 (s, 2H).

Step 2: Synthesis of the Compound 3

Sodium hydride (9.60 g, 240.02 mmol, a content of 60%) was slowly added to a solution of ethanol (144.00 mL) and tetrahydrofuran (432.00 mL), and the system was stirred at room temperature for 5 min. To the system were then added diethyl malonate (18.22 g, 113.75 mmol) and the compound 2 (39.00 g, 113.75 mmol). The system was stirred at room temperature for 30 min. After the reaction was completed, the mixture was quenched by adding water and concentrated under reduced pressure. The residue was purified by column chromatography to give the compound 3 as a colorless oil. $^1$H NMR (400 MHz, DMSO-d$_6$) δ 7.36 (s, 1H), 7.34-7.32 (m, 1H), 7.22-7.12 (m, 1H), 4.13 (q, J=14.0 Hz, J2=7.2 Hz, 6H), 1.18-1.14 (m, 8H).

Step 3: Synthesis of the Compound 4

To a solution of the compound 3 (10.00 g, 29.31 mmol) in water (10.00 mL) and DMSO (100.00 mL) was added lithium chloride (7.45 g, 175.86 mmol), and the system was stirred at 160° C. for 4 hours. After the reaction was completed, 100 mL of water was added, and the system was extracted with ethyl acetate (50 mL×5). The organic layer was washed with aqueous sodium bicarbonate solution (50 mL×2), dried over anhydrous sodium sulfate, and filtered. The filtrate was concentrated under reduced pressure. The residue was purified by column chromatography (petroleum ether:ethyl acetate=10:1) to give the compound 4 as a yellow oil. $^1$H NMR (400 MHz, DMSO-d$_6$) δ 7.40 (s, 1H), 7.29 (d, J=8.0 Hz, 1H), 7.15 (d, J=8.0 Hz, 1H), 4.07 (t, J=14.0 Hz, 2H), 3.42-3.35 (m, 1H), 3.16-3.04 (m, 4H), 1.18 (t, J=15.6 Hz, 3H).

Step 4: Synthesis of the Compound 5

A solution of the compound 4 (3.50 g, 13.00 mmol) and tributyl(pyridin-2-yl)stannane in toluene (50.00 mL) was purged three times with nitrogen. Tetra(triphenylphosphino) palladium (901.67 mg, 780.00 μmol) was then added to the reaction solution, and the system was stirred at 110° C. under nitrogen for 5 hours. After the reaction was completed, the reaction mixture was concentrated under reduced pressure, and the residue was purified by column chromatography (petroleum ether:ethyl acetate=3:1) to give the compound 5 as a light-yellow solid. $^1$H NMR (400 MHz, DMSO-d$_6$) δ 8.62 (d, J=6.4 Hz, 1H), 7.92-7.81 (m, 4H), 7.29 (d, J=5.2 Hz, 2H), 4.09 (q, J1=18.0 Hz, J2=6.8 Hz, 2H), 3.40-3.23 (m, 1H), 3.21-3.15 (m, 4H), 1.20 (t, J=14.4 Hz, 3H).

Step 5: Synthesis of the Compound 6

To a solution of the compound 5 (2.00 g, 7.48 mmol) in ethanol (20 mL) and water (5 mL) was added sodium hydroxide (1.50 g, 37.41 mmol) at 20° C., and the system was stirred at 20° C. for 30 minutes. After the reaction was completed, the reaction solution was concentrated to dryness. The solid was dissolved in 20 mL of water. The solution was acidified to pH 4-6, and extracted with ethyl acetate. The organic phase was dried over anhydrous sodium sulfate, filtered, and concentrated to give the compound 6 as a light-yellow oil. $^1$H NMR (400 MHz, DMSO-d$_6$) δ 8.63 (d, J=4.4 Hz, 1H), 7.94-7.83 (m, 3H), 7.34-7.31 (m, 2H), 3.30-3.00 (m, 1H), 3.22-3.16 (m, 4H).

Step 6: Synthesis of the Compound 8

To a solution of the compound 6 (200.00 mg, 835.88 μmol) and the compound 7 (207.90 mg, 1.00 mmol) in DMF were added EDCI (192.29 mg, 1.00 mmol) and HOBt (135.53 mg, 1.00 mmol), and the system was stirred at 50° C. for 6 hours. After the reaction was completed, the reaction mixture was concentrated under reduced pressure to dryness, and the residue was purified by preparative chromatography to give the compound 8 as a white solid. $^1$H NMR (400 MHz, CDCl$_3$) δ 8.70 (d, J=4.0 Hz, 1H), (s, 1H), 7.81-7.71 (m, 3H), 7.34 (d, J=8.0 Hz, 1H), 7.26-7.25 (m, 1H), (s, 2H), 3.91-3.83 (m, 1H), 3.79 (s, 3H), 3.45-3.35 (m, 4H), 2.60 (s, 3H).

Step 7: Preparation of the Compound of Formula (I)

The compound 8 (690.00 mg, 1.61 mmol) was chirally resolved by supercritical fluid chromatography (instrument: SFC-10; Chiral column: AD (250 mm*50 mm, 10 μm); Mobile phase: supercritical $CO_2$/MeOH (0.1% of $NH_3H_2O$) =55/45, flow rate: 180 mL/min; Column temperature: 38° C.), to give the compound of formula (I), and the retention time was about 1.7 min. $^1$H NMR (400 MHz, DMSO-$d_6$) δ 8.62 (d, J=3.2 Hz, 1H), (m, 4H), 7.63 (s, 2H), 7.34-7.29 (m, 2H), 4.09-4.06 (m, 1H), 3.74 (s, 3H), (m, 4H), 2.45 (s, 3H).

Example 2: Preparation of the Crystal Form A of the Compound of Formula (I)

About 20 g of the compound of formula (I) was weighted and added to 800 mL of ethanol. The mixture was stirred overnight with a magnetic stirrer. The mixture was filtered, the filter cake was rinsed with a small amount of ethanol, and the resulting solid was dried under reduced pressure. XRPD detection showed that the crystal form A of the compound of formula (I) was obtained.

Example 3: Preparation of the Crystal Form B of the Compound of Formula (II)

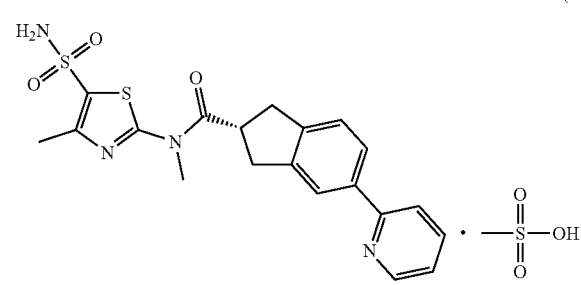

The compound of formula (I) (56.5 g, 131.85 mmol) was weighted and added to a round bottom flask (3 L), to which 2 L of anhydrous tetrahydrofuran was then added. The mixture was heated to 50-55° C. so that it was completely dissolved. The mixture was filtered. Methanesulfonic acid (12.67 g, 131.85 mmol) diluted with 50 mL of anhydrous tetrahydrofuran was added dropwise to the filtrate at 55° C. A solid precipitated out, and the mixture was further stirred for 2 hours. The mixture was filtered, and the filter cake was dried under reduced pressure. The resulting solid was added to a round bottom flask, to which 1 L of anhydrous ethanol was then added. The mixture was heated to 40° C. and stirred for 14 hours. The mixture was filtered, and the filter cake was dried under vacuum. XRPD detection showed that the crystal form B of the compound of formula (II) was obtained.

Example 4: Study on the Hygroscopicity of the Crystal Form B of the Compound of Formula (II)

Materials of the Assay:
SMS DVS Advantage dynamic vapor sorption apparatus
Method of the Assay:
10-15 mg of the crystal form B of the compound of formula (II) was taken and put into a DVS sample pan for testing.

Figure 7:
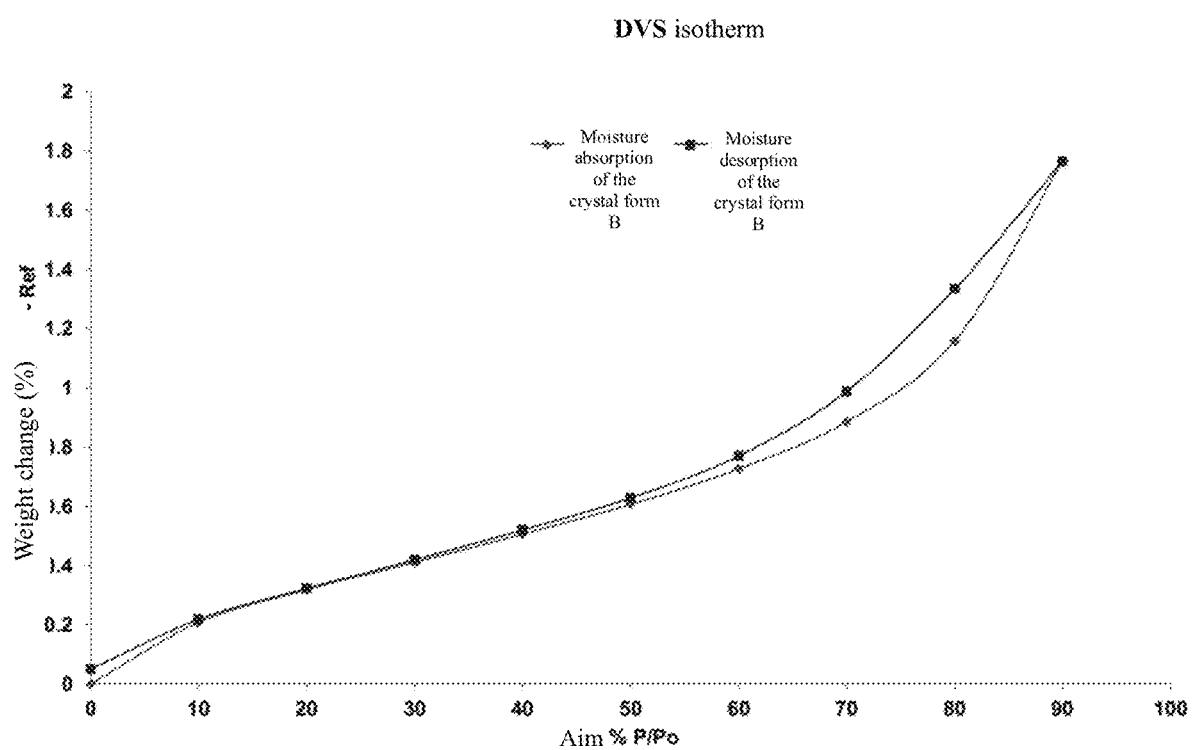
FIG. 7 is the DVS isotherm of the crystal form B of the compound of formula (II).

Results of the Assay:
The DVS spectrum of the crystal form B of the compound of formula (II) was shown in FIG. 7, wherein ΔW is 1.158%.
Conclusion of the Assay:
The weight increase by moisture absorption of the crystal form B of the compound of formula (II) at 25° C. and 80% RH was 1.158%, indicating that the crystal form B of the compound of formula (II) was slightly hygroscopic.

Assay Example 1: Assay of Cytopathic Effect of Herpes Simplex Virus-1 (Evaluation In Vitro)

Object of the Assay:
The assay of cytopathic effect (CPE) was used to determine the antiviral activity of the compound against the GHSV-UL 46 strain of herpes simplex virus-1 (HSV-1).
Instruments of the Assay:
Cell incubator: Thermo 2401
Cell counter: Beckman Vi-Cell™ XR
Automatic dispenser: Thermo Multidrop
Liquid transfer system for compound: Labcyte ECHO 555 liquid handler
Microplate reader: Molecular Device SpectraMax340PC384.
Materials of the Assay:
Virus: HSV-1 GHSV-UL46, ATCC #VR-1544
Cell: African green monkey kidney cell, Vero E6, donated by Wuhan Instititute of Virology, Chinese Academy of Sciences.
Reagents of the Assay:

| Name of reagent | Brand and number |
|---|---|
| DMEM, a cell culture medium | Gibco # 11995-065 |
| Fetal bovine serum | Corning # 35-076-CV |
| Double antibody | HyClone # SV30010 |
| Non-essential amino acids (NEAA) | Gibco # 11140050, 100× |
| Phosphate buffer | Corning # 21-031-CVR |
| Cell counting kit-8 (CCK8) | Biolite # 35004 |

Medium Preparation Method:
Cell growth medium: 500 ml of DMEM medium+50 ml of fetal bovine serum+5 ml of double antibody+5 ml of non-essential amino acids.
Medium for the assay of cytopathic effect: 500 ml of DMEM medium+10 ml of fetal bovine serum+5 ml of double antibody+5 ml of non-essential amino acids.
Steps of the Assay:
1. Cell plating (Day 1)
1.1 The work surface of the biological safety cabinet was wiped with 75% alcohol; the biological safety cabinet was irradiated with ultraviolet light for 15 minutes; the fan was turn on; and the glass window was stretched to the lower edge of the warning line, which was maintained for 5 minutes to stabilize the airflow in the cabinet.
1.2. A flask (T 150 cell culture flask) of Vero E6 cells with the cell density of 80% was taken out. The growth medium was aspirated out, and the cells were washed twice with 10 ml of phosphate buffer. 2 ml of trypsin was added, and the cells were put in a $CO_2$ incubator at 37° C. for digestion.
1.3. After the cells were separated and fallen off, 15 ml of the medium for the assay of cytopathic effect was added to stop the digestion; the cells were pipetted several times, and 1 ml of cell suspension was taken and counted with a cell counter.
1.4. The cells were diluted to $1.33×10^5$ cells/ml with the medium for the assay of cytopathic effect. The diluted cell suspension was added to a 384-well plate (Corning #3701) with 30 µl of 4000 cells per well by Multidrop.

1.5. The periphery of the cell plate was slightly shaken to make the cells evenly distributed, and the cell plate was then put in a $CO_2$ cell incubator at 37° C. and incubated overnight.

2. Compound dilution, treatment and virus inoculation (Day 2)

2.1. The compound was diluted in gradients with DMSO, and the diluted compound was added to the ECHO plate.

2.2. The compound was added to the 384-well plate seeded with cells with the ECHO 555 liquid workstation. Each test compound was measured at 8 concentrations in duplicate. For cell control wells, no compound and virus were added. For virus control wells, no compound was added. The final concentration of DMSO in all wells was 0.5%.

2.3. The virus was diluted with the assay medium, and inoculated at 1.5 $TCID_{90}$/well, 30 µl. The assay medium was added with Multidrop to cell control wells, 30 µl per well. The diluted virus was then added with Multidrop to compound test wells and virus control wells, 30 µl per well.

2.4. The cell plate was put in a $CO_2$ cell incubator at 37° C., and incubated for 5 days.

3. Cell viability test (Day 7)

3.1. After 5 days of culture, cytopathic changes were observed in all wells of the cell plate. The cells in the control wells should not be diseased, while almost all the cells in the virus control wells were diseased.

3.2. CCK8 was added to the cell plate with Multidrop, 6 µl per well.

3.3. The cell plate was put in a $CO_2$ cell incubator at 37° C., and incubated for 3 hours.

3.4. The absorbance value of each well of the cell plate was read with a microplate reader at a wavelength of 450 nm, and 630 nm was used as a reference wavelength. The value of raw data was the absorbance at 450 nm minus the absorbance at 630 nm (raw data=$OD_{450}-OD_{630}$).

4. Data analysis 4.1. The antiviral activity of the test compound (% Inhibition) was calculated using the following equation:

$$\% \text{ Inhibition} = \left(\frac{\text{sample} - \text{virus control}}{\text{cell control} - \text{virus control}}\right) \times 100$$

wherein sample is the absorbance value of compound test wells, cell control is the average absorbance value of cell control wells, and virus control is the average absorbance value of virus control wells.

4.2. The dose-response curve was plotted using the GraphPad Prism software, and the half-effective concentration ($EC_{50}$) of the test compound was obtained.

5. The results of the assay are shown in Table 3.

TABLE 3

Test results of HSV-1 cytopathic assay

| Compound No. | HSV-1 Cytopathic Assay $EC_{50}$ (µM) |
|---|---|
| Compound of formula (I) | 0.007 |

6. Conclusion: The compound of the disclosure has good antiviral activity against herpes simplex virus (HSV).

Assay Example 2: Evaluation of Pharmacokinetics of the Compound

Object of the assay: to test the pharmacokinetics of the compound in mice in vivo.

Materials of the Assay:
Balb/c mice (male, 18-22 g, 6-8 weeks old, from Shanghai SLAC)

Procedures of the Assay:
The pharmacokinetic profile of the compound after intravenous injection and oral administration in the rodents was tested by the standard protocol. The candidate compound was formulated into a corresponding solution, and administered through a single intravenous injection (1.0 mg/kg, 5% of DMSO/95% of 20% hydroxypropyl-beta-cyclodextrin) or an intragastric administration (1.0 mg/kg, 0.5% of methylcellulose MC4000). The whole blood sample was collected within 24 hours, and centrifuged at 3000 g for 15 minutes. The supernatant was separated to give the plasma sample, and 4 times volume of acetonitrile solution containing an internal standard was added to precipitate the proteins. The resulting mixture was centrifuged and the supernatant was taken out, to which an equal volume of water was added and centrifuged. The supernatant was taken out, and injected as a sample to quantitatively analyze the plasma drug concentration by LC-MS/MS analysis method. The pharmacokinetic parameters were calculated, such as peak concentration, peak time, clearance rate, half-life, area under the drug-time curve, bioavailability, etc.

The results of the assay are shown in Table 4:

TABLE 4

The results of the pharmacokinetic assay

| Test product (compound prepared in each example) | Clearance rate (mL/min/kg) | Half-life $T_{1/2}$ (h) | Concentration integral AUC (nM · hr) | Bioavailability F (%) |
|---|---|---|---|---|
| | Parameters of intravenous administration | | Parameters of oral administration | |
| Control (Pritelivir) | 0.4 | 6 | 128921 | 100 |
| Compound of formula (I) | 1.2 | 6 | 24371 | 75 |

Conclusion: The compound of the present disclosure shows lower plasma exposure and better safety at the same effective dose in the study of pharmacokinetics in vivo of intragastric administration in mice.

What is claimed is:

1. A crystal form A of compound of formula (I), wherein the X-ray powder diffraction pattern thereof has characteristic diffraction peaks at the following 2θ angles: 10.81±0.2°, 15.97±0.2°, and 21.69±0.2°,

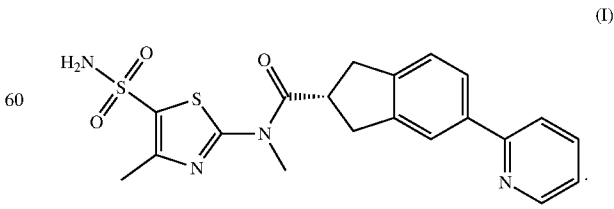

(I)

2. The crystal form A according to claim 1, wherein the X-ray powder diffraction pattern thereof has characteristic diffraction peaks at the following 2θ angles: 10.81±0.2°, 13.03±0.2°, 15.97±0.2°, 18.48±0.2°, 21.69±0.2°, 23.78±0.2°, 25.14±0.2°, and 26.96±0.2°.

3. The crystal form A according to claim 2, wherein the XRPD pattern thereof is shown in FIG. 1.

4. The crystal form A according to claim 1, wherein the differential scanning calorimetry curve thereof has a starting point of the endothermic peak at 216.04±3° C.

Figure 2:
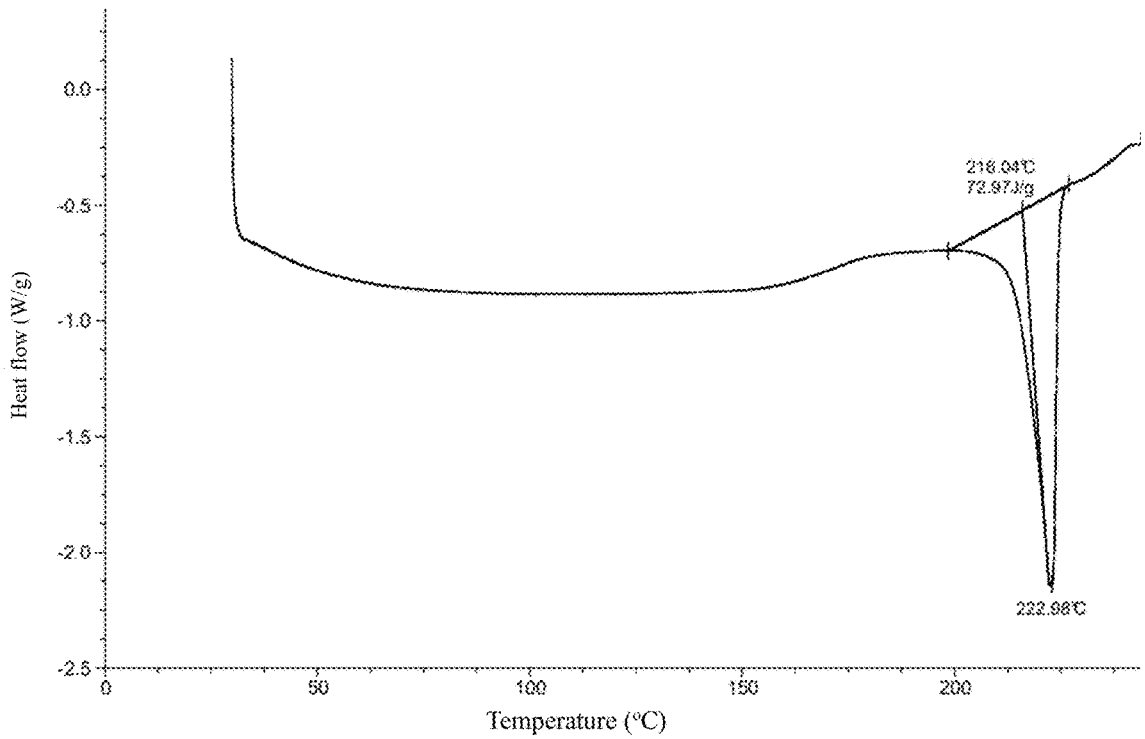
FIG. 2 is the DSC curve of the crystal form A of the compound of formula (I)

5. The crystal form A according to claim 4, wherein the DSC curve thereof is shown in FIG. 2.

6. The crystal form A according to claim 1, wherein the thermogravimetric analysis curve thereof has a weight loss of up to 0.4442% at 120±3° C. and up to 2.4492% at 204±3° C.

Figure 3:
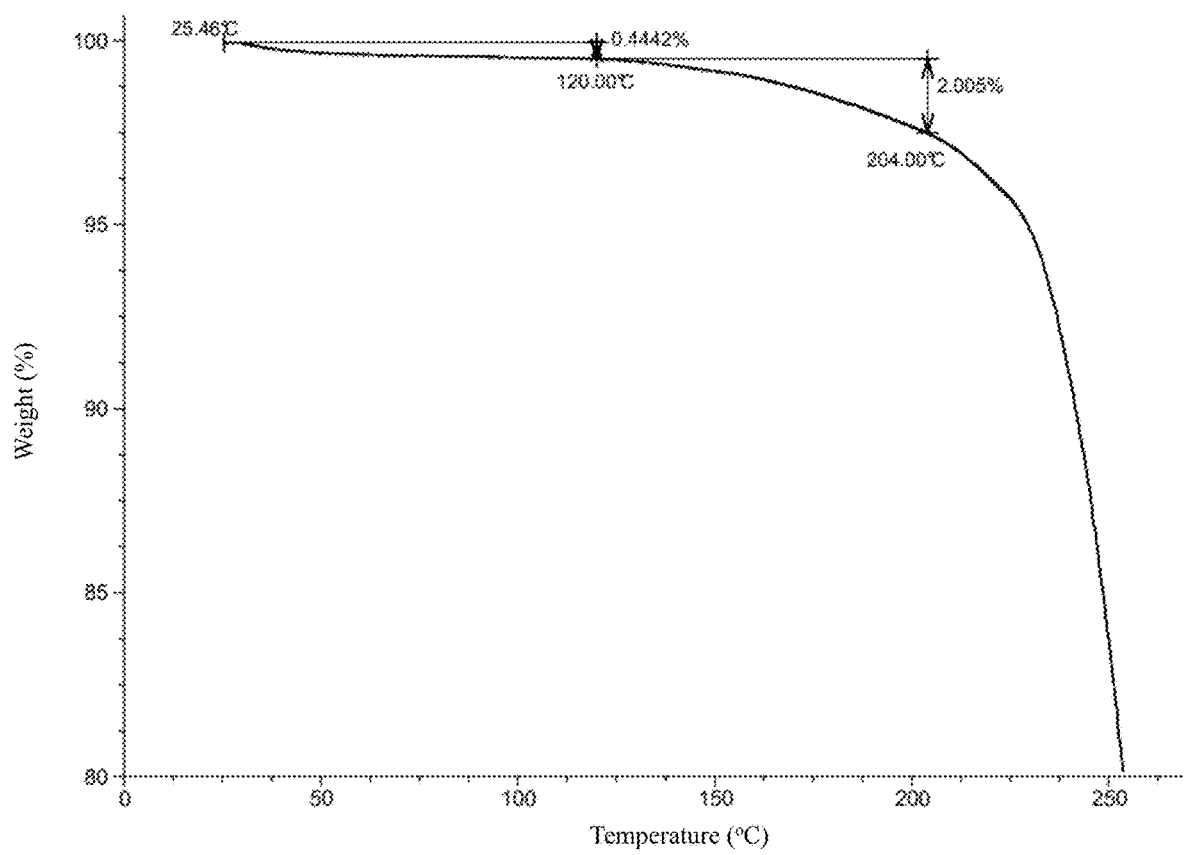
FIG. 3 is the TGA curve of the crystal form A of the compound of formula (I)

7. The crystal form A according to claim 6, wherein the TGA curve thereof is shown in FIG. 3.

8. A crystal form B of a compound of formula (II),

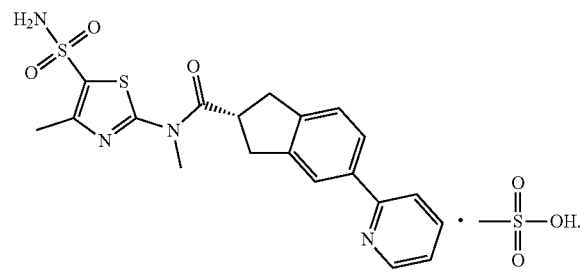

wherein the X-ray powder diffraction pattern thereof has characteristic diffraction peaks at the following 2θ angles: 10.17±0.2°, 11.85±0.2°, and 15.94±0.2°.

9. The crystal form B according to claim 8, wherein the X-ray powder diffraction pattern thereof has characteristic diffraction peaks at the following 2θ angles: 8.46±0.2°, 10.17±0.2°, 11.85±0.2°, 13.98±0.2°, 15.94±0.2°, 20.39±0.2°, 21.32±0.2°, and 23.78±0.2°.

Figure 4:
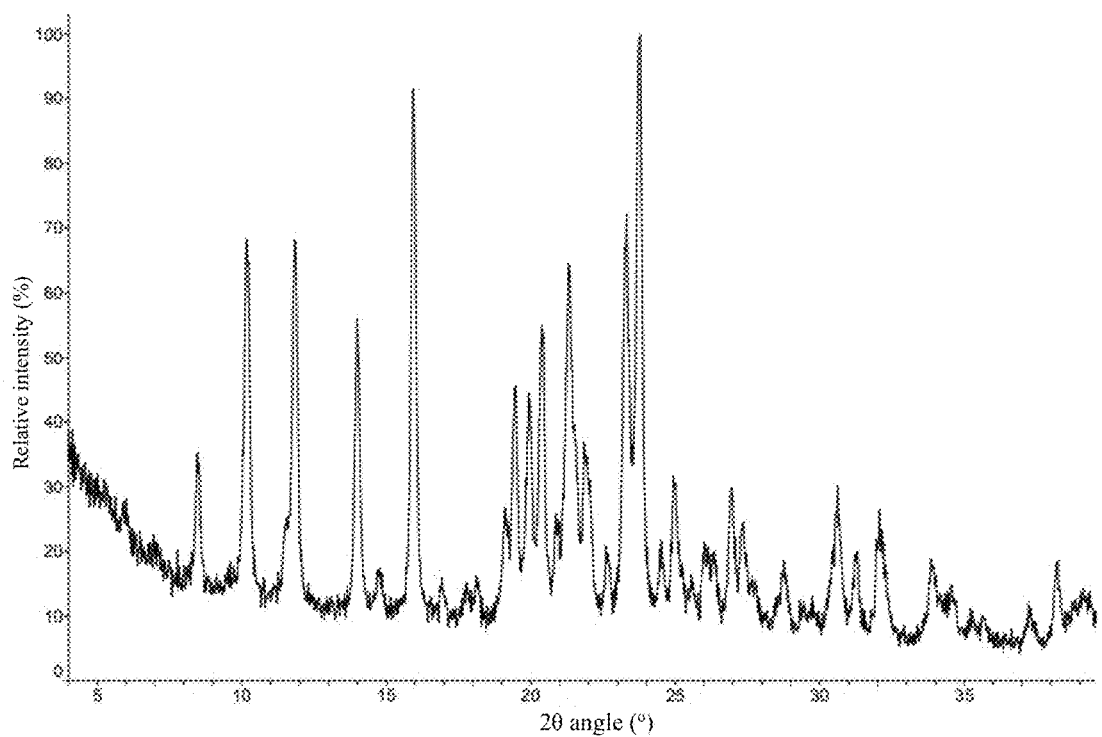
FIG. 4 is the XRPD pattern of the crystal form B of the compound of formula (II) using Cu-Kα radiation.

10. The crystal form B according to claim 9, wherein the XRPD pattern thereof is shown in FIG. 4.

11. The crystal form B according to 8, wherein the differential scanning calorimetry curve thereof has a starting point of the endothermic peak at 185.89±3° C.

Figure 5:
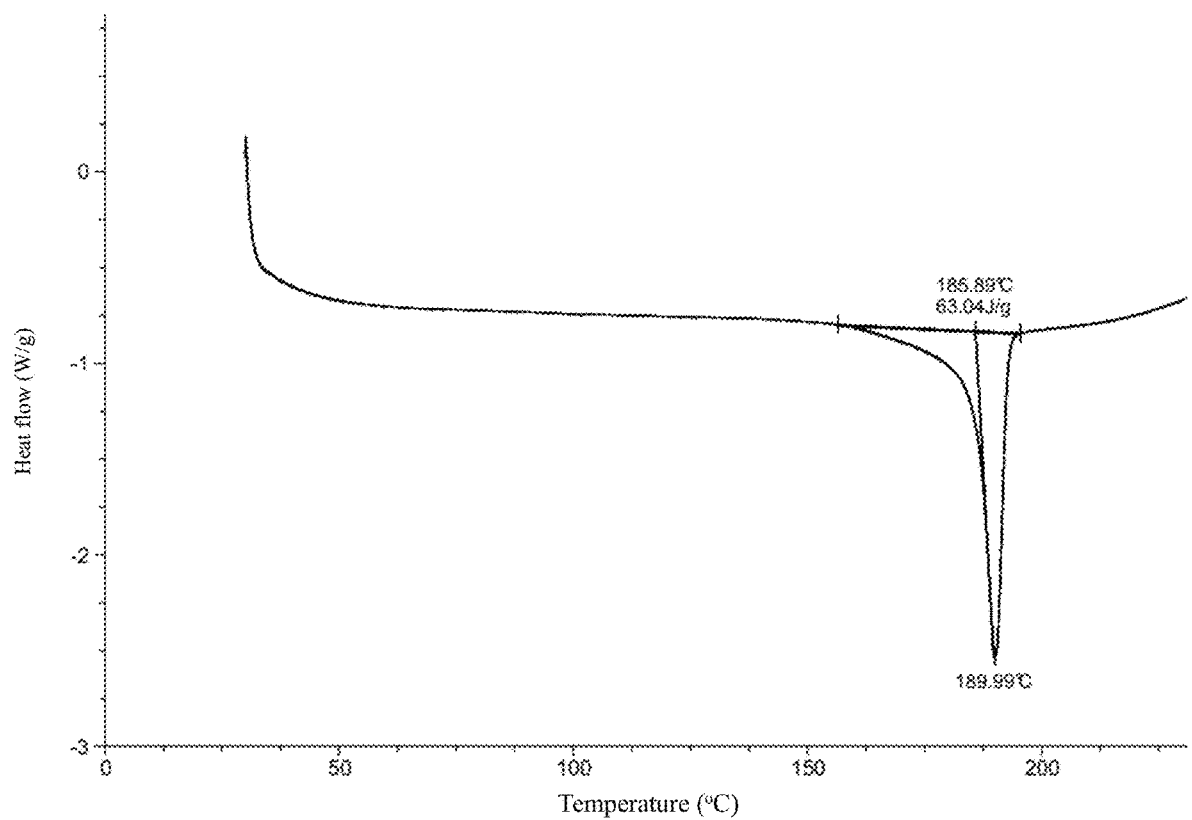
FIG. 5 is the DSC curve of the crystal form B of the compound of formula (II)

12. The crystal form B according to claim 11, wherein the DSC curve thereof is shown in FIG. 5.

13. The crystal form B according to claim 8, wherein the thermogravimetric analysis curve thereof has a weight loss of up to 0.7160% at 187.16±3° C.

Figure 6:
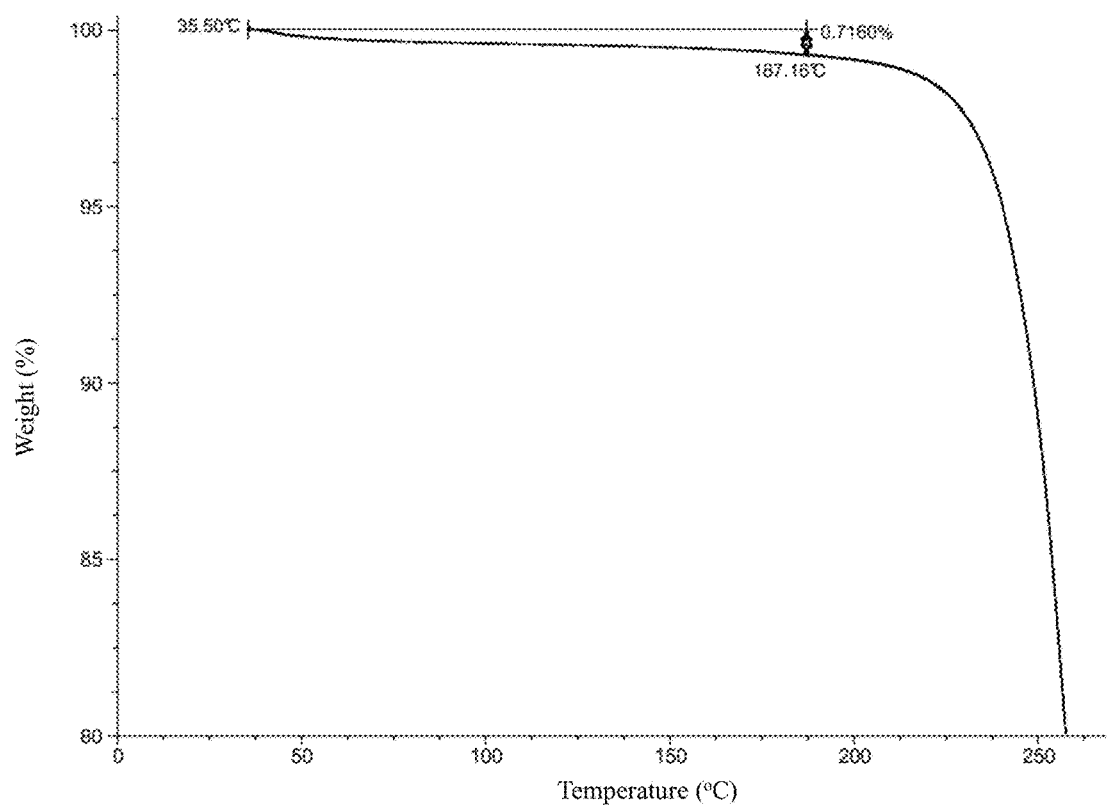
FIG. 6 is the TGA curve of the crystal form B of the compound of formula (II)

14. The crystal form B according to claim 13, wherein the TGA curve thereof is shown in FIG. 6.

15. A method of treating a disease related to herpes simplex virus in a subject in need thereof, comprising administering to the subject the crystal form A of the compound of formula (I) according to claim 1.

16. A method of treating a disease related to herpes simplex virus in a subject in need thereof, comprising administering to the subject the crystal form B of the compound of formula (II) according to claim 8.

17. The crystal form A according to claim 4, wherein the thermogravimetric analysis curve thereof has a weight loss of up to 0.4442% at 120±3° C. and up to 2.4492% at 204±3° C.

18. The crystal form B according to claim 11, wherein the thermogravimetric analysis curve thereof has a weight loss of up to 0.7160% at 187.16±3° C.

* * * * *